(12) United States Patent
Wehner et al.

(10) Patent No.: US 7,972,530 B2
(45) Date of Patent: Jul. 5, 2011

(54) DEICING AND ANTI-ICING COMPOSITIONS COMPRISING RENEWABLY-BASED, BIODEGRADABLE 1,3-PROPANEDIOL

(75) Inventors: Ann Wehner, Hockessin, DE (US); Gyorgyi Fenyvesi, Wilmington, DE (US); Robert Miller, Wilmington, DE (US); Joseph W. DeSalvo, Lafayette Hill, PA (US); Melissa Joerger, Newark, DE (US)

(73) Assignee: DuPont Tate & Lyle Bio Products Company, LLC, Wilmington, DE (US)

( * ) Notice: Subject to any disclaimer, the term of this patent is extended or adjusted under 35 U.S.C. 154(b) by 0 days.

(21) Appl. No.: 12/427,232

(22) Filed: Apr. 21, 2009

(65) Prior Publication Data

US 2009/0218541 A1 Sep. 3, 2009

Related U.S. Application Data

(63) Continuation of application No. 11/705,275, filed on Feb. 12, 2007, now abandoned.

(60) Provisional application No. 60/772,471, filed on Feb. 10, 2006, provisional application No. 60/772,194, filed on Feb. 10, 2006, provisional application No. 60/772,193, filed on Feb. 10, 2006, provisional application No. 60/772,111, filed on Feb. 10, 2006, provisional application No. 60/772,120, filed on Feb. 10, 2006, provisional application No. 60/772,110, filed on Feb. 10, 2006, provisional application No. 60/772,112, filed on Feb. 10, 2006, provisional application No. 60/846,948, filed on Sep. 25, 2006, provisional application No. 60/853,920, filed on Oct. 24, 2006, provisional application No. 60/859,264, filed on Nov. 15, 2006, provisional application No. 60/872,705, filed on Dec. 4, 2006, provisional application No. 60/880,824, filed on Jan. 17, 2007.

(51) Int. Cl.
*C09K 3/18* (2006.01)

(52) U.S. Cl. ............ 252/70; 106/13
(58) Field of Classification Search .......... 252/70; 106/13

See application file for complete search history.

(56) References Cited

U.S. PATENT DOCUMENTS

| | | | |
|---|---|---|---|
| 3,392,135 | A | 7/1968 | Holub |
| 4,404,184 | A | 9/1983 | Pittet et al. |
| 4,486,334 | A | 12/1984 | Horiuchi et al. |
| 4,897,220 | A | 1/1990 | Trieselt et al. |
| 5,286,512 | A | 2/1994 | Klemann et al. |
| 5,403,508 | A | 4/1995 | Reng et al. |
| 5,441,662 | A | 8/1995 | Schwadtke et al. |
| 5,716,604 | A | 2/1998 | Coe et al. |
| 5,716,676 | A | 2/1998 | Schutze et al. |
| 5,932,532 | A | 8/1999 | Ghosh et al. |
| 5,968,407 | A * | 10/1999 | Boluk et al. ............ 252/70 |
| 6,123,932 | A | 9/2000 | Guskey et al. |
| 6,174,521 | B1 | 1/2001 | Li et al. |
| 6,245,879 | B1 | 6/2001 | Kelsey et al. |
| 6,255,442 | B1 | 7/2001 | Kurian et al. |
| 6,551,640 | B1 | 4/2003 | Drantch et al. |
| 6,589,926 | B1 | 7/2003 | Vinson et al. |
| 7,323,539 | B2 | 1/2008 | Sunkara et al. |
| 7,419,655 | B2 | 9/2008 | Malik |
| 2003/0082756 | A1 | 5/2003 | Burch et al. |
| 2004/0076684 | A1 | 4/2004 | Lin |
| 2005/0009721 | A1 | 1/2005 | Delplancke et al. |
| 2005/0020805 | A1 | 1/2005 | Sunkara et al. |
| 2005/0069997 | A1 * | 3/2005 | Adkesson et al. ......... 435/158 |
| 2005/0154147 | A1 | 7/2005 | Germroth et al. |
| 2007/0037926 | A1 | 2/2007 | Olsen et al. |
| 2007/0107080 | A1 | 5/2007 | Liao et al. |
| 2008/0166448 | A1 | 7/2008 | Wittorff et al. |

FOREIGN PATENT DOCUMENTS

| | | |
|---|---|---|
| EP | 0562773 | 9/1993 |
| EP | 0620971 | 10/1994 |
| EP | 1564225 | 8/2005 |
| EP | 1604647 | 12/2005 |
| JP | 2002138069 | 5/2002 |
| WO | WO9921736 | 5/1999 |
| WO | WO9960849 | 12/1999 |
| WO | WO0000568 | 1/2000 |
| WO | WO02073727 | 9/2002 |

OTHER PUBLICATIONS

Galinsky, et al., "Basic Pharmacokinetics and Pharmacodynamics" in: Remington: The Science and Practice of Pharmacy (Baltimore, Lippincott williams & Wilkins, 2006) p. 1171.
Abstract: Blomstrom et al. Nature 1980, 283, pp. 66-83; 1 Page.
Thwaites (The Wisconsin Magazine of History 1952, 35(4), p. 277.
Jabrane, et al., "Study of the Thermal Behaviour of 1,3-Propanediol and its Aqueous Solutions", Thermochimica Acta 311 (1998); pp. 121-127.
Al-Hasani, S., et al., "Successful embryo transfer of cryopreserved and in-vitro fertilized rabbit oocytes"; Human Reproduction, vol. 4, No. 1, 1989, pp. 77-79.
Chen, et al., "Cyclization During Polyesterifications: Isolation of an 18-Member Ring Compound from Reaction of Phthalic Anhydride with 2,2-Dimethyl-1,3-Propanediol", Journal of Applied Polymer Science, 1990, vol. 41, Issue 9-10, pp. 2517-2520.
Cameron, D.C., et al., "Metabolic Engineering of Propanediol Pathways", Biotechnol. Prog., 1998, vol. 14, No. 1, pp. 119-125.
Hermann, B.G., et al., "Today's and Tomorrow's Bio-Based Bulk Chemicals from White Biotechnology", Applied Biochemistry and Biotechnology, vol. 136, 2007, pp. 361-388.

(Continued)

*Primary Examiner* — Anthony J Green
(74) *Attorney, Agent, or Firm* — McCarter & English

(57) ABSTRACT

Disclosed herein are deicing and anti-icing compositions comprising 1,3-propanediol, wherein the 1,3-propanediol in said deicing or anti-icing composition has a bio-based carbon content of about 1% to 100%. In addition, it is preferred that the 1,3-propanediol be biologically-derived, and wherein upon biodegradation, the biologically-derived 1,3-propanediol contributes no anthropogenic $CO_2$ emissions to the atmosphere.

10 Claims, 3 Drawing Sheets

OTHER PUBLICATIONS

News Release, DuPont Tate & Lyle Bio Products Begin Bio-PDO Production in Tennessee, Loudon, Tennessee Nov. 27, 2006, 3 pages.
Straitman, Rick, "DuPont Makes Key Polymer Ingredient from Corn Instead of Petroleum", May 1, 2001, Wilmington, Delaware, 2 Pages.

Fung, et al., "Evolution of Carbon Sinks in a Changing Climate", PNAS, Aug. 9, 2005, vol. 12, No. 32, pp. 11201-11206.
"Industrial Bioproducts: Today and Tomorrow" (Paster, et al.) Prepared by Energetics, Inc. for the US Department of Energy, Jul. 2003, See p. 1 and 2, Table 1-1 and 1-6.

* cited by examiner

FIGURE 3

| Product | Molecular weight | product | product | $CO_2$ fixated | $CO_2$ released | net atmospheric $CO_2$ released |
|---|---|---|---|---|---|---|
| | g/mol | kg | mol | mol | mol | kg |
| EG | 62.068 | 1 | 16.1 | 0.0 | 32.2 | 1.4 |
| PG | 76.094 | 1 | 13.1 | 0.0 | 39.4 | 1.7 |
| Chem-PDO | 76.094 | 1 | 13.1 | 0.0 | 39.4 | 1.7 |
| Bio-PDO™ | 76.094 | 1 | 13.1 | 39.4 | 39.4 | 0.0 |

DEICING AND ANTI-ICING COMPOSITIONS COMPRISING RENEWABLY-BASED, BIODEGRADABLE 1,3-PROPANEDIOL

CROSS REFERENCE TO RELATED APPLICATIONS

The present application claims the benefit of U.S. Provisional Application Ser. No. 60/772,471, filed Feb. 10, 2006; U.S. Provisional Application No. 60/772,194, filed Feb. 10, 2006, U.S. Provisional Application No. 60/772,193, filed Feb. 10, 2006, U.S. Provisional Application No. 60/772,111, filed Feb. 10, 2006, U.S. Provisional Application No. 60/772,120, filed Feb. 10, 2006, U.S. Provisional Application No. 60/772,110, filed Feb. 10, 2006, U.S. Provisional Application No. 60/772,112, filed Feb. 10, 2006, U.S. Provisional Application No. 60/846,948, filed Sep. 25, 2006, U.S. Provisional Application No. 60/853,920, filed Oct. 24, 2006, U.S. Provisional Application No. 60/859,264, filed Nov. 15, 2006, U.S. Provisional Application No. 60/872,705, filed Dec. 4, 2006, U.S. Provisional Application No. 60/880,824, filed Jan. 17, 2007, and is a continuation of U.S. application Ser. No. 11/705,275, filed Feb. 12, 2007 which is currently abandoned, the disclosure of which is expressly incorporated herein by reference in its entirety.

FIELD OF THE INVENTION

Disclosed herein are deicing and anti-icing compositions comprising 1,3-propanediol wherein the 1,3-propanediol in said deicing and anti-icing composition has a bio-based carbon content of about 1% to 100%. In addition, it is preferred that the 1,3-propanediol be biologically-derived, and wherein upon biodegradation, the biologically-derived 1,3-propanediol contributes no anthropogenic $CO_2$ emissions to the atmosphere.

BACKGROUND OF THE INVENTION

Consumers of deicing and anti-icing compositions consider many factors in selecting products for use. Recently certain factors have been a focus of and have driven scientific study and product development. These driving factors include, product safety, environmental impact, the extent to which the components are natural, and the aesthetic quality of the overall product. Therefore, manufacturers have to be concerned with the environmental impact of their products. In fact, the effort towards environmental impact awareness is a universal concern, recognized by government agencies. The Kyoto Protocol amendment to the United Nations Framework Convention on Climate Change (UNFCCC) currently signed by 156 nations is one example of a global effort to favor safer environmental manufacturing over cost and efficiency. When applied to deicing and anti-icing, consumers are increasingly selective about the origins of the products they purchase. The 2004 Co-operative Bank's annual Ethical Consumerism Report (www.co-operativebank.co.uk) disclosed a 30.3% increase in consumer spending on ethical retail products (a general classification for environmental safe, organic and fair trade goods) between 2003 and 2004 while total consumer spending during the same period rose only 3.7%.

Glycols such as ethylene glycol, propylene glycol, 1,3-butylene glycol, and 2-methyl-1,3-propanediol are biodegradable compounds useful in compositions ranging from cosmetics and personal care formulations to detergents to heat transfer compositions. While biodegradability is an important factor in protecting the environment, biodegradation of glycols derived from fossil-based sources has the unavoidable consequence of releasing previously fixed CO2 into the atmosphere. Thus, while glycols in general are advantageous for their biodegradability, the resulting global warming potential of fossil-based glycols during biodegradation is significant.

Carbon dioxide is singled out as the largest component of the collection of greenhouse gases in the atmosphere. The level of atmospheric carbon dioxide has increased 50% in the last two hundred years. Recent reports indicate that the current level of atmospheric carbon dioxide is higher than the peak level in the late Pleistocene, the epoch before modern humans (Siegenthaler, U. et al. Stable Carbon Cycle-Climate Relationship During the Late Pleistocene, Science, Vol. 310, no. 5752 (Nov. 25, 2005), pp. 1313-1317). Therefore, any further addition of carbon dioxide to the atmosphere is thought to further shift the effect of greenhouse gases from stabilization of global temperatures to that of heating. Consumers and environmental protection groups alike have identified industrial release of carbon into the atmosphere as the source of carbon causing the greenhouse effect.

Greenhouse gas emission can occur at any point during the lifetime of a product. Consumers and environmental groups consider the full lifespan of a product when evaluating a product's environmental impact. Consumers look for products that do not contribute new carbon to the atmosphere considering the environmental impact of production, use and degradation. Only organic products composed of carbon molecules from plant sugars and starches and ultimately atmospheric carbon are considered to not further contribute to the greenhouse effect.

In addition to adding carbon dioxide to the atmosphere, current methods of industrial production of glycols produce contaminants and waste products that include among them sulfuric acid, hydrochloric acid, hydrofluoric acid, phosphoric acid, oxalic acid tartaric acid, acetic acids, Alkali metals, alkaline earth metals, transitional metals and heavy metals, including Iron, cobalt, nickel, copper, silver, molybdenum, tungsten, vanadium, chromium, rhodium, palladium, osmium, iridium, rubidium, and platinum (U.S. Pat. Nos. 2,434,110, 5,034,134, 5,334,778, and 5,10,036).

Also of concern to consumers, especially consumers of deicing and anti-icing products, is an individual's reaction to such a product. The rate of development of hypersensitivity has markedly increased in the US in the last two decades. Many of these reactions are attributed to trace amount of substances. Other reactions are of idiopathic origin. Consumers seek products that are composed of ingredients of a more purified source and/or of all natural composition.

SUMMARY OF THE INVENTION

The present invention is directed to a deicing or anti-icing composition comprising 1,3-propanediol and an aqueous solution, wherein said 1,3-propanediol has a bio-based carbon content of at least 1%.

The present invention is further directed to a deicing or anti-icing composition comprising 1,3-propanediol and a surfactant, wherein said 1,3-propanediol has a bio-based carbon content of at least 1%.

The present invention is also directed to a deicing or anti-icing composition comprising 1,3-propanediol wherein said 1,3-propanediol has an ultraviolet absorption at 220 nm of less than about 0.200 and at 250 nm of less than about 0.075 and at 275 nm of less than about 0.075.

The present invention is additionally directed to a deicing or anti-icing composition comprising 1,3-propanediol wherein said 1,3-propanediol has a concentration of total organic impurities of less than about 400 ppm.

The present invention is even further directed to a deicing or anti-icing composition comprising 1,3-propanediol, wherein the 1,3-propanediol in said composition has an anthropogenic $CO_2$ emission profile of zero upon biodegradation.

BRIEF DESCRIPTION OF THE DRAWINGS

FIG. 3 is a table that shows the calculations for the data shown in FIGS. 1 and 2.

DETAILED DESCRIPTION OF THE INVENTION

Figure 1:
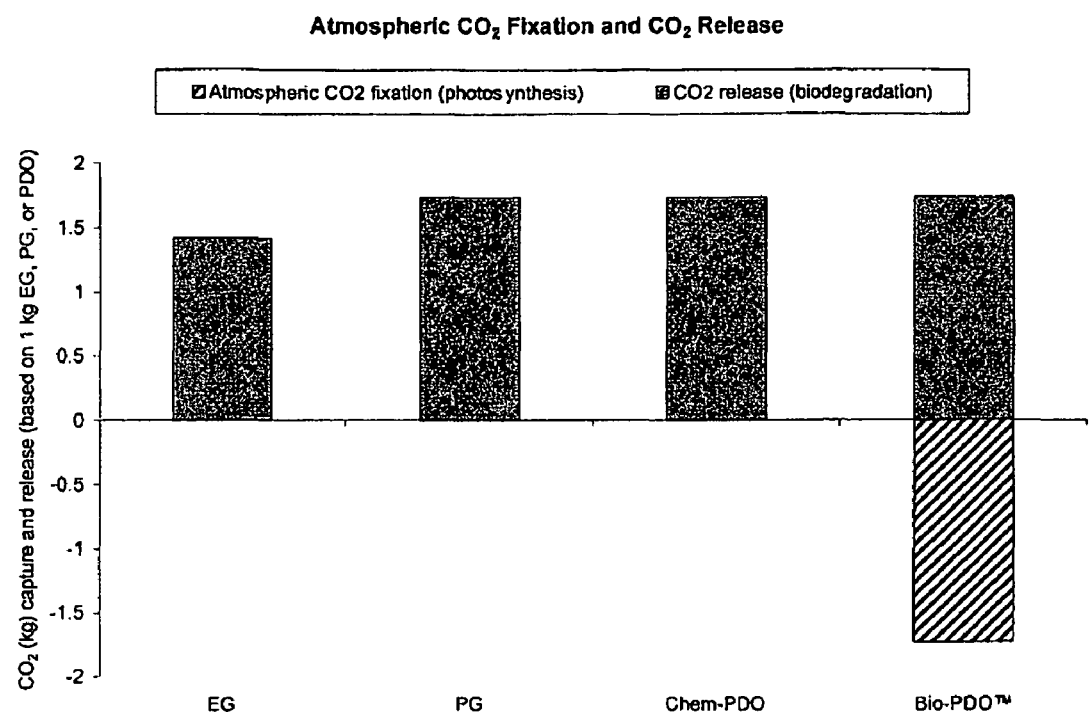
FIG. 1 is a graph showing $CO_2$ emissions for $CO_2$ fixation from the atmosphere during photosynthesis for renewably based 1,3-propanediol (Bio-PDO™) (−1.7 kg $CO_2$/kg product) and $CO_2$ release to the atmosphere during biodegradation (kg $CO_2$/kg product) for ethylene glycol (EG) (+1.4 kg $CO_2$/kg product), propylene glycol (PG) (+1.7 kg $CO_2$/kg product), fossil-based 1,3-propanediol (Chem-PDO) (+1.7 kg $CO_2$/kg product), and fermentatively-derived 1,3-propanediol (Bio-PDO™) (+1.7 kg $CO_2$/kg product).
Figure 2:
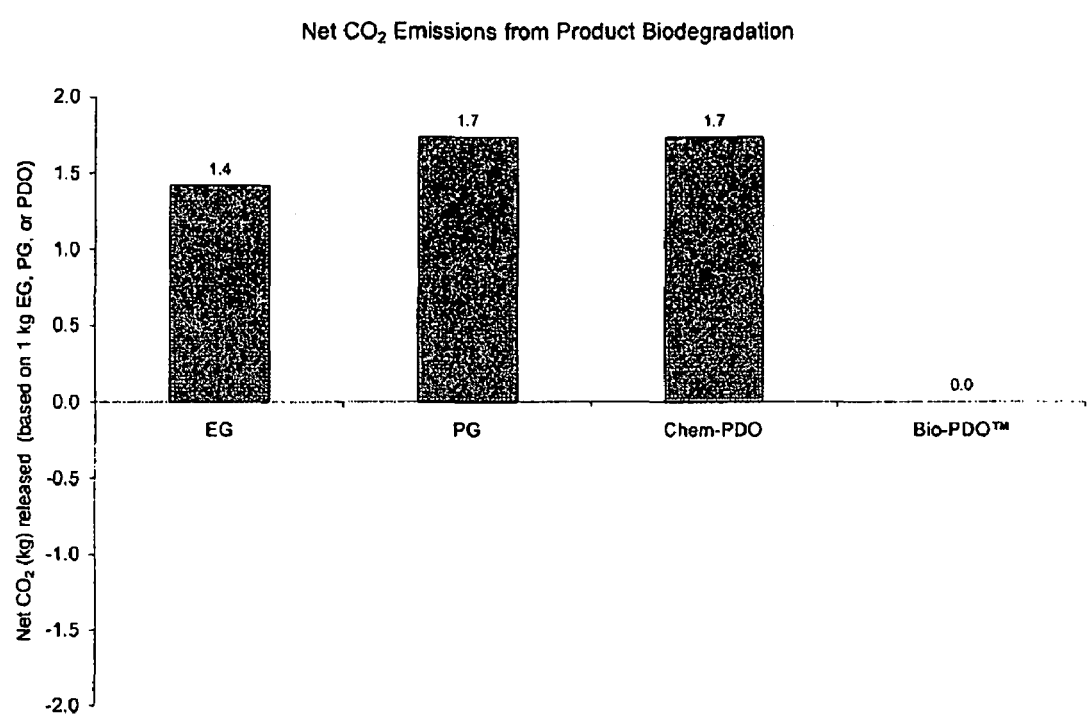
FIG. 2 is a graph showing that the net emissions of $CO_2$ to the atmosphere for renewably based 1,3-propanediol (Bio-PDO) is zero (0).

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Compositions disclosed herein comprise 1,3-propanediol, having at least 1% bio-based carbon content, as greater as up to 100% of the glycol component of the composition. In one embodiment, the 1,3-propanediol comprises substantially all of the glycol component of the composition of the invention. In another embodiment, the 1,3-propanediol comprises all of the glycol component of the composition.

1,3-Propanediol

The terms "bioPDO", "biologically-derived, biodegradable 1,3-propanediol", "biologically derived 1,3-propanediol", "renewably-based 1,3-propanediol", "renewably-based, biodegradable 1,3-propanediol," "biosourced, and "biologically-produced 1,3-propanediol" and similar terms as used here in refer to 1,3-propanediol derived from microorganism metabolism of plant-derived sugars composed of carbon of atmospheric origin, and not composed of fossil-fuel carbon.

Anthropogenic $CO_2$ Emission Profile

Applicants' invention relates to deicing and anti-icing compositions comprising renewably-based, biodegradable 1,3-propanediol, in which said renewably-based, biodegradable 1,3-propanediol has an anthropogenic $CO_2$ emission profile of zero (0). An "anthropogenic emission profile" means anthropogenic $CO_2$ emissions that are contributed to the atmosphere upon biodegradation of a compound or composition. p "Biodegradable" or "Biodegradability" means the capacity of a compound to be broken down by living organisms to simple, stable compounds such as carbon dioxide and water.

Whereas photosynthesis is the process of creating growing matter through the conversion of carbon dioxide ($CO_2$) and water ($H_2O$) into plant material through the action of the sun, biodegradation is the process of converting organic material back into $CO_2$ and $H_2O$ through the activity of living organisms.

There are many published test methods for measuring the biodegradability of organic chemicals such as glycols. One internationally recognized method is ASTM E1720-01, Standard Test Method for Determining Ready, Ultimate Biodegradability of Organic Chemicals in a Sealed Vessel $CO_2$ Production Test.

Chemicals that demonstrate 60% biodegradation or better in this test method will biodegrade in most aerobic environments and are classified as ready biodegradable. All of the glycols referred to in this document meet this criteria.

Calculations setting forth the finding that the 1,3-propanediol of the present invention provides no anthropogenic COs emissions upon biodegradation is set forth below. A table in support of these calculations is provided in FIG. 3.

When one molecule of 1,3-propanediol degrades, three molecules of $CO_2$ are released into the atmosphere. Because all of these molecules of $CO_2$ released during degradation from "fermentatively-derived" 1,3-propanediol have an atmospheric origin, the net release of $CO_2$ to the atmosphere is thus zero. Comparatively, because a fossil fuel-derived propylene glycol and fossil-derived 1,3-propanediol contains three carbon atoms which originate from a fixed carbon source (i.e., the fossil fuel), degradation of one molecule of fossil fuel-derived propylene glycol or 1,3-propanediol results in a net release of three molecules of $CO_2$ into the atmosphere. Similarly, because fossil fuel-derived ethylene glycol contains two carbon atoms, which originate from a fixed carbon source, degradation of one molecule of fossil fuel-derived ethylene glycol results in a net release of two molecules of $CO_2$ into the atmosphere.

In order to quantify the $CO_2$ released for one kilogram of each ethylene glycol, propylene glycol, chemical 1,3-propanediol and "fermentatively-derived" 1,3 propanediol (Bio-PDO™), the product weight (1 kg) is divided by its molecular weight. For each carbon atom present in the molecule, one molecule of $CO_2$ is released. The molecules of $CO_2$ are multiplied by the molecular weight of $CO_2$ (44 kg/kmole) to quantify the impact of $CO_2$ release (kg) per one unit (kg) of product.

Fossil-Fuel Based Carbon Feedstock Release 1 kg of fossil fuel derived ethylene glycol*(1 kmol EG/62.068 kg)*(2 kmol $CO_2$/1 kmol EG)*(44 kg $CO_2$/kmol $CO_2$)=1.4 kg $CO_2$ 1 kg of fossil fuel derived propylene glycol*(1 kmol PG/76.094 kg)*(3 kmol $CO_2$/1 kmol PG)*(44 kg $CO_2$/kmol $CO_2$)=1.7 kg $CO_2$ 1 kg of fossil fuel derived 1,3-propanediol*(1 kmol chem-PDO/76,094 kg*(3 kmol $CO_2$/1 kmol chem-PDO)*(44 kg $CO_2$/kmol $CO_2$)=1.7 kg $CO_2$ Bio-Based Carbon Feedstock Balance Capture:

1 kg of Bio-PDO™*(1 kmol Bio-PDO™/76.094 kg)* (−3 kmol $CO_2$/1 kmol Bio-PDO™)*(44 kg $CO_2$/kmol $CO_2$)=−1.7 kg $CO_2$ Release:

1 kg of Bio-PDO™*(1 kmol Bio-PDO™/76.094 kg)*(3 kmol $CO_2$/1 kmol Bio-PDO™)*(44 kg $CO_2$/kmol $CO_2$)=1.7 kg $CO_2$ Net:

1.7 kg+1.7 kg=0 kg

This Bio-based Carbon Feedstock Balance result demonstrates that there are no anthropogenic CO2 emissions from the biodegradation of the renewably sourced Bio-PDO. The term "anthropogenic" means man-made or fossil-derived.

Bio-Based Carbon

"Carbon of atmospheric origin" as used herein refers to carbon atoms from carbon dioxide molecules that have recently, in the last few decades, been free in the earth's atmosphere. Such carbons in mass are identifiable by the present of particular radioisotopes as described herein. "Green carbon", "atmospheric carbon", "environmentally friendly carbon", "life-cycle carbon", "non-fossil fuel based carbon", "non-petroleum based carbon", "carbon of atmospheric origin", and "biobased carbon" are used synonymously herein.

"Carbon of fossil origin" as used herein refers to carbon of petrochemical origin. Such carbon has not been exposed to UV rays as atmospheric carbon has, therefore masses of carbon of fossil origin has few radioisotopes in their population. Carbon of fossil origin is identifiable by means described herein. "Fossil fuel carbon", "fossil carbon", "polluting carbon", "petrochemical carbon" "petro-carbon" and carbon of fossil origin are used synonymously herein.

The abbreviation "IRMS" refers to measurements of CO2 by high precision stable isotope ratio mass spectrometry.

The term "carbon substrate" means any carbon source capable of being metabolized by a microorganism wherein the substrate contains at least one carbon atom.

"Renewably-based" denotes that the carbon content of the 1,3-propanediol is from a "new carbon" source as measured by ASTM test method D 6866-05 Determining the Biobased Content of Natural Range Materials Using Radiocarbon and Isotope Ratio Mass Spectrometry Analysis, incorporated herein by reference. This test method measures the C-14/C-12 isotope ratio in a sample and compares it to the C-14/C-12 isotope ratio in a standard 100% biobased material to give percent biobased content of the sample. "Biobased materials" are organic materials in which the carbon comes from recently (on a human time scale) fixated $CO_2$ present in the atmosphere using sunlight energy (photosynthesis). On land, this $CO_2$ is captured or fixated by plant life (e.g., agricultural crops or forestry materials). In the oceans, the $CO_2$ is captured or fixated by photosynthesizing bacteria or phytoplankton. A biobased material has a C-14/C-12 isotope ratio in range of from 1:0 to greater than 0:1. Contrarily, a fossil-based material, has a C-14/C-12 isotope ratio of 0:1.

A small amount of the carbon dioxide in the atmosphere is radioactive. This 14C carbon dioxide is created when nitrogen is struck by an ultra-violet light produced neutron, causing the nitrogen to lose a proton and form carbon of molecular weight 14 which is immediately oxidized in carbon dioxide. This radioactive isotope represents a small but measurable fraction of atmospheric carbon. Atmospheric carbon dioxide is cycled by green plants to make organic molecules during the process known as photosynthesis. The cycle is completed when the green plants or other forms of life metabolize the organic molecules producing carbon dioxide which is released back to the atmosphere. Virtually all forms of life on Earth depend on this green plant production of organic molecule to produce the chemical energy that facilitates growth and reproduction. Therefore, the 14C that exists in the atmosphere becomes part of all life forms, and their biological products. These renewably based organic molecules that biodegrade to CO2 do not contribute to global warming as there is no net increase of carbon emitted to the atmosphere. In contrast, fossil fuel based carbon does not have the signature radiocarbon ratio of atmospheric carbon dioxide.

Atmospheric origin and fixed carbon source as used herein are relative terms in that the time period of when CO2 is of atmospheric or fixed origin relates to the life cycle of the 1,3-propanediol. Thus, while it is quite possible that, at one time, carbon from a fossil fuel was found in the atmosphere (and, as a corollary, that atmospheric CO2 may one day be incorporated into a fixed carbon source), for purposes herein carbon is considered to be from a fixed carbon source until it is released into the atmosphere by degradation.

Assessment of the renewably based carbon in a material can be performed through standard test methods. Using radiocarbon and isotope ratio mass spectrometry analysis, the biobased content of materials can be determined. ASTM International, formally known as the American Society for Testing and Materials, has established a standard method for assessing the biobased content of materials The ASTM method is designated ASTM-D6866.

The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modem reference standard. The ratio is reported as a percentage with the units "pMC" (percent modern carbon). If the material being analyzed is a mixture of present day radiocarbon and fossil carbon (containing no radiocarbon), then the pMC value obtained correlates directly to the amount of Biomass material present in the sample.

The modern reference standard used in radiocarbon dating is a NIST (National Institute of Standards and Technology) standard with a known radiocarbon content equivalent approximately to the year AD 1950. AD 1950 was chosen since it represented a time prior to thermo-nuclear weapons testing which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. It's gradually decreased over time with today's value being near 107.5 pMC, This means that a fresh biomass material such as corn could give a radiocarbon signature near 107.5 pMC.

Combining fossil carbon with present day carbon into a material will result in a dilution of the present day pMC content. By presuming 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, it would give a radiocarbon signature near 54 pMC.

A biomass content result is derived by assigning 100% equal to 107.5 pMC and 0% equal to 0 pMC. In this regard, a sample measuring 99 pMC will give an equivalent biobased content result of 93%.

A sample of "fermentatively-derived" 1,3-propanediol was submitted by DuPont to Iowa State University for bio-based content analysis using ASTM method D 6866-05. The results received from Iowa State University demonstrated that the above sample was 100% bio-based content (ref: Norton, Glenn. Results of Radiocarbon Analyses on samples from DuPont Bio-Based Materials—reported Jul. 8, 2005).

Assessment of the materials described herein were done in accordance with ASTM-D6866. The mean values quoted in this report encompasses an absolute range of 6% (plus and minus 3% on either side of the biobased content value) to account for variations in end-component radiocarbon signatures. It is presumed that all materials are present day or fossil in origin and that the desired result is the amount of biobased component "present" in the material, not the amount of bio-based material "used" in the manufacturing process.

Results of Radiocarbon Analyses on Samples from DuPont Bio-Based

| Materials Reported Jul. 08, 2005 | |
| --- | --- |
| PRODUCT | BIOBASED CONTENT (%) |
| 1,3-Propanediol | 100 |

There may be certain instances wherein a deicing or anti-icing composition of the invention may comprise a combination of a biologically-derived 1,3-propanediol and one or more non biologically-derived glycol components, such as, for example, chemically synthesized 1,3-propanediol. In such occasions, it may be difficult, if not impossible to determine which percentage of the glycol composition is biologically-derived, other than by calculating the bio-based carbon content of the glycol component. In this regard, in the deicing and anti-icing compositions of the invention, the glycol component, and in particular, the 1,3-propanediol, can comprise at least about 1% bio-based carbon content up to 100% bio-based carbon content, and any percentage therebetween.

Purity

"Substantially purified," as used by applicants to describe the biologically-produced 1,3-propanediol produced by the process of the invention, denotes a composition comprising 1,3-propanediol having at least one of the following characteristics: 1) an ultraviolet absorption at 220 nm of less than about 0.200 and at 250 nm of less than about 0.075 and at 275 nm of less than about 0.075; or 2) a composition having L*a*b* "b*" color value of less than about 0.15 and an absorbance at 270 nm of less than about 0.075; or 3) a peroxide composition of less than about 10 ppm; or 4) a concentration of total organic impurities of less than about 400 ppm.

A "b*" value is the spectrophotometrically determined "Yellow Blue measurement as defined by the CIE L*a*b* measurement ASTM D6290.

The abbreviation "AMS" refers to accelerator mass spectrometry.

By the acronym "NMR" is meant nuclear magnetic resonance.

By the terms "color" and "color bodies" is meant the existence of visible color that can be quantified using a spectrocolorimeter in the range of visible light, using wavelengths of approximately 400-800 nm, and by comparison with pure water. Reaction conditions can have an important effect on the nature of color production. Examples of relevant conditions include the temperatures used, the catalyst and amount of catalyst. While not wishing to be bound by theory, we believe color precursors include trace amounts of impurities comprising olefinic bonds, acetals and other carbonyl compounds, peroxides, etc. At least some of these impurities may be detected by such methods as UV spectroscopy, or peroxide titration.

"Color index" refers to an analytic measure of the electromagnetic radiation-absorbing properties of a substance or compound.

Biologically-derived 1,3-propanediol useful in deicing and anti-icing compositions disclosed herein has at least one of the following characteristics: 1) an ultraviolet absorption at 220 nm of less than about 0.200 and at 250 nm of less than about 0.075 and at 275 nm of less than about 0.075; or 2) a composition having L*a*b* "b*" color value of less than about 0.15 and an absorbance at 270 nm of less than about 0.075; or 3) a peroxide composition of less than about 10 ppm; or 4) a concentration of total organic impurities of less than about 400 ppm. A "b*" value is the spectrophotometrically determined Yellow Blue measurement as defined by the CIE L*a*b* measurement ASTM D6290.

The level of 1,3-propanediol purity can be characterized in a number of different ways. For example, measuring the remaining levels of contaminating organic impurities is one useful measure. Biologically-derived 1,3-propanediol can have a purity level of less than about 400 ppm total organic contaminants; preferably less than about 300 ppm; and most preferably less than about 150 ppm. The term ppm total organic purity refers to parts per million levels of carbon-containing compounds (other than 1,3-propanediol) as measured by gas chromatography.

Biologically-derived 1,3-propanediol can also be characterized using a number of other parameters, such as ultraviolet light absorbance at varying wavelengths. The wavelengths 220 nm, 240 nm and 270 nm have been found to be useful in determining purity levels of the composition. Biologically-derived 1,3-propanediol can have a purity level wherein the UV absorption at 220 nm is less than about 0.200 and at 240 nm is less than about 0.075 and at 270 nm is less than about 0.075.

Biologically-derived 1,3-propanediol can have a b* color value (CIE L*a*b*) of less than about 0.15.

The purity of biologically-derived 1,3-propanediol compositions can also be assessed in a meaningful way by measuring levels of peroxide. Biologically-derived 1,3-propanediol can have a concentration of peroxide of less than about 10 ppm.

It is believed that the aforementioned purity level parameters for biologically-derived and purified 1,3-propanediol (using methods similar or comparable to those disclosed in U.S. Patent Application No. 2005/0069997) distinguishes such compositions from 1,3-propanediol compositions prepared from chemically purified 1,3-propanediol derived from petroleum sources, as per the prior art.

Fermentation

"Biologically produced" means organic compounds produced by one or more species or strains of living organisms, including particularly strains of bacteria, yeast, fungus and other microbes. "Bio-produced" and biologically produced are used synonymously herein. Such organic compounds are composed of carbon from atmospheric carbon dioxide converted to sugars and starches by green plants.

"Biologically-based" means that the organic compound is synthesized from biologically produced organic components. It is further contemplated that the synthesis process disclosed herein is capable of effectively synthesizing other monoesters and diesters from bio-produced alcohols other than 1,3-propanediol; particularly including ethylene glycol, diethylene glycol, triethylene glycol, 1,2-propylene glycol, dipropylene diol, tripropylene diol, 2-methyl 1,3-propanediol, neopentyl glycol and bisphenol A. "Bio-based", and "bio-sourced"; "biologically derived"; and "bio-derived" are used synonymously herein.

"Fermentation" as used refers to the process of metabolizing simple sugars into other organic compounds. As used herein fermentation specifically refers to the metabolism of plant derived sugars, such sugar are composed of carbon of atmospheric origin.

Biologically-derived 1,3-propanediol can be obtained based upon use of the fermentation broth ("fermentatively-derived") generated by a genetically-engineered *Eschericia coli* (*E. coli*) previously disclosed in, for example, U.S. Pat. No. 5,686,276. However, other single organisms, or combinations of organisms, may be used to biologically produce 1,3-propanediol, using organisms that have been genetically-engineered according to methods known in the art. "Fermentation" refers to a system that catalyzes a reaction between substrate(s) and other nutrients to product(s) through use of a biocatalyst. The biocatalysts can be a whole organism, an isolated enzyme, or any combination or component thereof that is enzymatically active. Fermentation systems useful for producing and purifying biologically-derived 1,3-propanediol are disclosed in, for example, Published U.S. Patent Application No. 2005/0069997 incorporated herein by reference.

The biologically derived 1,3-propanediol (Bio-PDO) for use in the current invention, produced by the process described herein, contains carbon from the atmosphere incorporated by plants, which compose the feedstock for the production of Bio-PDO. In this way, the Bio-PDO used in the compositions of the invention contains only renewable carbon, and not fossil fuel based, or petroleum based carbon. Therefore the compositions of the invention have less impact on the environment as the propanediol used in the compositions does not deplete diminishing fossil fuels and, upon degradation releases carbon back to the atmosphere for use by plants once again. Thus, the present invention can be characterized as more natural and having less environmental impact than similar compositions comprising petroleum based glycols.

Moreover, as the purity of the Bio-PDO utilized in the compositions of the invention is higher than chemically synthesized 1,3-propanediol and other glycols, risk of introducing impurities that may cause irritation is reduced by its use over commonly used glycols, such as propylene glycol.

This 1,3-propanediol of the invention can be isolated from the fermentation broth and is incorporated into deicing and anti-icing compositions of the invention, by processes as are known to those of ordinary skill in the applicable art.

Renewably-Based, Biodegradable 1,3-propanediol-Containing Compositions

As mentioned above, Bio-PDO can be incorporated into numerous compositions as a glycol component. For example, Bio-PDO can be part of or the sole glycol component of deicing compositions and anti-icing compositions.

It is contemplated herein that other renewably-based or biologically-derived glycols, such as ethylene glycol or 1,2 propylene glycol, diethylene glycol, triethylene glycol among others, can be used in the anti-icing and deicing compositions of the present invention.

The deicing/anti-icing compositions can be used in any application requiring deicing and/or anti-icing. In some embodiments, the compositions are used for the removal of, and/or time-limited protection against, deposits of frost, ice, and/or snow on exterior aircraft surfaces prior to take off, or on roadway/runway surfaces. The compositions can be applied through a commercial deicing/anti-icing vehicle system to the surfaces at pressures and flow rates normal for intended use.

In addition to application to aircraft, the compositions can also be used for other anti-icing/deicing applications, such as, surfaces of, for example, airport pavements, roadways, walkways, sidewalks, bridges, entrances, electrical tower structures and their components, electricity transmission lines, canals, locks, vessels, nautical components, railroad switches, and motor vehicles. In addition, the compositions can be used in applications such as birdbaths, outdoor fountains, decorative ponds, and other outdoor areas where water freezing would be aesthetically or functionally unacceptable. In these applications the fluids can prevent water from freezing during the winter in cold climates with reduced biological risk to wildlife or domestic animals.

It is also envisioned that the compositions of the present invention can be used in either a liquid or a solid format. For instance, the compound can be prepared as a liquid and sprayed on or spread on surfaces. Alternatively, it can be prepared in a solid form and employed as a powder. Optionally, the solid may be further processed using methods well known in the art, such as, for example, pelletizing, prilling, flaking, or macerating to provide the formulation in a final useable powdered or granular form. Any of the binders known to those skilled in the art optionally may be present and may either be inert or may be comprised of components that actively help lower the freezing point. For example, cinders, sawdust, sand, gravel, sugars, maltodextrins and mixtures thereof and the like can be used.

In the methods of the present invention, the deicing and/or anti-icing compositions of the present invention are applied, such as by spraying or injecting for liquid forms.

In the anti-icing or deicing compositions of the invention, the Bio-PDO or other bio-derived glycol component can be the major component of the composition, present in amounts up to 100% by weight based on the weight of the total composition. The amount of Bio-PDO used in the products is generally the balance after adding one or more of surfactant, corrosion inhibitors, water, and any optional ingredients. Deicing/anti-icing fluids preferably contain from about 10% to about 95% Bio-PDO by weight, and more preferably from about 25% to about 92%. A typical formulation for aircraft deicing/anti-icing may include, but is not limited to, the following components: 25-95% by weight of Bio-PDO or mixture thereof; and up to 1% each of the following components: at least one surfactant or surfactant blend, at least one corrosion inhibitor, a pH control agent, a thickening agent, and a dye. Water can make up the balance of this formulation. Further details on alternative formulations and ingredients is provided below.

In certain embodiments, such as those containing glycerol in combination with Bio-PDO, the compositions of the invention preferably contain from about 10% to about 88% glycerol and as such, from as little as about 1% to about 30% Bio-PDO.

Functional and Other Ingredients

The deicing/anti-icing products of the invention can include one or more functional and other ingredients. Functional and other ingredients useful herein may be categorized or described herein by their benefit or their postulated mode of action in the deicing or anti-icing composition. However, it is to be understood that the functional and other ingredients useful herein can in some instances provide more than one benefit or operate via more than one mode of action. Therefore, classifications herein are made for the sake of convenience and are not intended to limit an ingredient to the particularly stated application or applications listed.

Surfactants

A preferred surfactant is a nonionic surfactant; anionic, cationic, and amphoteric (zwitterionic) surfactants are less preferred. Some nonlimiting examples of suitable nonionic surfactants are: alkylphenol ethoxylates ($C_{12}$ or lower, $C_8$ or lower preferred); fatty or oxo-alcohol polyethyleneglycol ethers ($C_{16}$ or lower, $C_6$ or lower preferred); ethylene oxide-propylene oxide polymers ($C_{80}$ or lower, $C_2$ or lower preferred); fatty alcohol polyglycol ethers ($C_{18}$ or lower, $C_8$ or lower preferred); polyethoxylates such as polyoxyethylene ethers; polypropyloxylates such as polyoxypropylene ethers; sugar-based surfactants such as alkyl glycosides (e.g., alkyl benzene and tert-butoxyethanol); ethers of $C_1$ to $C_8$ polyethylene oxide repeat units of 2 to 50 polyethylene oxide units (low carbon alkyl group and somewhat higher carbon ethoxylate group preferred); polyvinyl alcohols having MW 1000-10,000; and polyvinyl pyrrolidones.

The nonionic surfactants can be selected from polyoxyalkylene ethers. Some preferred polyoxyalkylene ethers are ethers of $C_{12}$ to $C_{18}$ alcohols with polyethylene oxide repeat units of 2 to 100 polyethylene oxide units. Such surfactants include, for example, the Brij™ series of surfactants manufactured by ICI (e.g., Brij 30, 35, 52, 56, 58, 72, 76, 78, 92, 97, 98 and 700). Brij 35 is polyoxyethylene lauryl ether, 718 average MW, having the chemical formula: $CH_3(CH_2)_{11}(CH_2CH_2O)_{xH}$, where x on average is 23.

The fluids can contain any suitable amount of surfactant. Preferably, the fluids contain from about 0.01% to about 0.9% surfactant by weight, and more preferably from about 0.05% to about 0.5%.

pH Control Agent

The deicing/anti-icing compositions of the invention can optionally include one or more pH control agents to maintain the fluid at constant pH. The compositions can have any suitable pH. The pH of the compositions can range anywhere from about 3.5 to about 12, and preferably from about 6 to about 9. The desired pH can be obtained using inorganic bases such as sodium hydroxide, ammonium hydroxide and potassium hydroxide, or amines such as triethanol amine, diethanol amine or monoethanol amine.

Some nonlimiting examples of suitable buffers include: phosphate salts ($K^+$, $NH_4^+$); pyrophosphates ($Na^+$, $K^+$, $NH_4^+$); metaphosphates ($Na^+$, $K^+$, $NH_4^+$); carbonic acid and its salts ($Na^+$, $K^+$, $NH_4^+$); hydroxylammonium ($Na^+$, $K^+$, $NH_4^+$); adidic acid and its salts ($Na^+$, $K^+$, $NH_4^+$); maleic acid and its salts ($Na^+$, $K^+$, $NH_4^+$); and ascorbic acid and its salts ($Na^+$, $K^+$, $NH_4^+$).

Defoamers

Defoamers may also be employed. Any commercially available defoamer or antifoamer can be used, but particularly preferred defoamers are a silicone defoamer of Union Carbide Corporation sold under the trademark SAG, and FOAMBAN™ defoamer available from Ultra Additives Inc., Patterson, N.J. The amount of defoamer to be used is preferably in the range of from about 0.05% to about 0.5% by weight based on the weight of the total composition.

Corrosion Inhibitors

Suitable corrosion inhibitors are known to the art, and typically comprise mixtures of various functional materials, e.g., buffers, chelating agents, and the like, esters of inorganic acids such as the phosphorus and boron, aromatic triazoles such as tolyl- and benzyltriazole, and the like, in one or more solvents. A preferred anticorrosion mixture is that product sold by Sandoz under the designation "Sandocorin 8132". Those having skill in the art understand that selection of appropriate corrosion inhibitor may be made based upon the type of surfaces which the present compositions are likely to come in contact with, and how long and under what conditions they are likely to remain on that surface.

Suitable corrosion inhibitors include those belonging to the group comprising inorganic metal salts, alkali metal salts of fatty acids, monoalkyl amines and dialkyl amines optionally alkoxylated—and salts thereof, alkanol amines—optionally alkoxylated and salts thereof, esters of phosphorus acid or of phosphoric acid, and triazoles. The amount of corrosion inhibitor to be used is preferably in the range of from about 0.05% to about 0.8% by weight based on the weight of the total composition.

Thickening Agents

Thickening agents can be used in the compositions of the invention, and often comprise polymeric water-activated thickening agents. Thickening agents will typically comprise between 0.1 and 15.0 weight percent of the total composition. Examples include polysaccharide thickeners, natural gum thickeners, marine algae colloids, and cellulose ether thickeners. A preferred thickener is a polysaccharide known generically as Xanthan Gum.

Oils

The composition can optionally contain at least one nonpolar oil, such as aliphatic and aromatic oils such as mineral oil, paraffin oil, silicone oil, and propylene oxide/ethylene oxide copolymers. The amount of such oils is frequently in the range of from about 0.01% to about 5% by weight based on the total weight of the composition. The preferred range is between 0.10/0 to 1.0% by weight based on the total weight of the composition.

Thermal Stabilizing Agents

The deicing/anti-icing products can further include a material that improves the thermal stability of the material. Any suitable material having these properties can be used, for example certain of the phosphate salts. A particular example is a mixture of mono-basic sodium phosphate and di-basic sodium phosphate, such as the monohydrate mono-basic and heptahydrate di-basic sodium phosphates.

The products can contain any suitable amount of the buffer/freezing point depressant. The fluids preferably contain from about 0.02% to about 2% mono-basic sodium phosphate and from about 0.02% to about 2% di-basic sodium phosphate by weight, more preferably from about 0.3% to about 1.5% mono-basic sodium phosphate and from about 0.3% to about 1.5% di-basic sodium phosphate.

Anti-Microbial Agents

The deicing/anti-icing products can optionally include one or more anti-microbial agents. Some nonlimiting examples of suitable anti-microbial agents include: sodium azide; quaternary ammonium compounds (e.g., 2-methyl-4,5-trimethylene-4-isothizoline-3-one; n-alkyl dimethyl benzyl ammonium $X^-$ [where alkyl carbon number is $C_{12-18}$]; n-alkyl trimethyl ammonium $X^-$ [where alkyl carbon number is $C_{12-18}$]; dialkyl dimethyl ammonium $X^-$ [where alkyl carbon number is $C_{12-18}$]; octyl decyl dimethyl ammonium×[where $X^-$ is $Cl^-$, $Br^-$, $I_3^-$, $HCO_3^-$, $CO_3^{2-}$, phosphates, phosphonates, OH, carboxylates, polycarboxylates]); $M^+$ benzoates (where $M^+$ is $Na^+$, $K^+$, $NH_4^+$; alkyl dimethyl benzyl ammonium chlorides; and alkyl dimethyl benzyl/ethyl benzyl ammonium chlorides.

Fire Retardants

The deicing/anti-icing products can also optionally include one or more flame and/or corrosion inhibitors. Some common additives used for both fire and corrosion inhibition include sodium tolyltriazole and 1H-benzotriazole, methyl.

Vinylpyrrolidone

In another embodiment of the invention, the deicing/anti-icing fluids include a biobased freezing point depressant as described above, in combination with a vinylpyrrolidone polymer having a molecular weight between about 10,000 and about 700,000, and water. By "vinylpyrrolidone polymer" is meant a homopolymer or a copolymer of vinylpyrrolidone, or a derivative thereof. Suitable derivatives of vinylpyrrolidine polymer may include alkylated polyvinylpyrrolidones, 2-menthyl. Preferably, the vinylpyrrolidone polymer is polyvinylpyrrolidone.

The vinylpyrrolidone polymer preferably has a molecular weight between about 10,000 and about 700,000, and preferably not greater than about 360,000. It is believed that higher molecular weight vinylpyrrolidone polymers may produce deicing/anti-icing fluids having less desirable properties, particularly for aircraft and runway deicing.

The deicing/anti-icing products can contain any suitable amount of the vinylpyrrolidone polymer. Typically, the products contain about 5% or less vinylpyrrolidone polymer, and usually between about 0.1% and about 3%.

Advantageously, the vinylpyrrolidone polymer often functions as both a thickener and a surfactant in the fluid. Consequently, products having desirable properties can be produced using a minimal number of ingredients. However, optionally the products can also contain other ingredients such as an antioxidant and/or a second surfactant.

Aqueous Solvents

The deicing/anti-icing products can also include an aqueous solvent (i.e. water) in any suitable amount, usually in an amount of from about 30% to about 70% by weight. It should be noted that the percentages of ingredients given herein are based on a ready-to-use products. The products of the invention can also be provided in a concentrate formulation, in which case the percentage of aqueous solvent will decrease (e.g., the concentrate may contain from about 5% to about 20% water) and the percentages of other materials will increase accordingly.

Colorants or Dyes

The deicing/anti-icing products can also include an colorants or dyes in any suitable amount, usually in an amount up to 0.25% by volume of the formulation.

Esters

Esters can function as many of the above noted ingredients. While those in those having skill in the art can readily determine which esters are most appropriate to provide a particularly desired function, applications specifically note that esters used in this invention may include the esters produced, including all the appropriate conjugate mono and diesters, from biologically-derived 1,3 propanediol using organic carboxylic acids. Some esters in particular that are produced include propanediol distearate and monostearate, propandiol dilaurate and monolaurate, propanediol dioleate and monooleate, propanediol divalerate and monovalerate, propanediol dicaprylate and monocaprylate, propanediol dimyristate and monomyristate, propanediol dipalmitate and monopalmitate, propanediol dibehenate and monobehenate, propanediol adipate, propanediol maleate, propanediol dioxalate, propanediol dibenzoate, propanediol diacetate, and all mixtures thereof.

Miscellaneous Additives

The composition may also contain various other functional ingredients such as UV inhibitors, odor-modification agents, stabilizers and the like. Each of these components will typically comprise less than 1.0 weight percent of the total composition.

In specific applications, certain embodiments of the present invention are especially preferred due to certain regulatory or industry guidelines. For example, in the deicing and/or anti-icing of aircraft, it is preferred to use deicing and/or anti-icing fluids of Bio-PDO, water; a mixture of Bio-PDO and other bio-derived glycols and water, or a mixture of Bio-PDO, petrochemically derived glycols, and water. agents of methyl glucoside; a mixture of sorbitol and Bio-PDO; or a mixture of methyl glucoside, sorbitol and Bio-PDO with sodium lactate and/or potassium lactate.

For the deicing and/or anti-icing of runways, it may be preferable to use deicing and/or anti-icing agents of sodium lactate; potassium lactate; a mixture of sodium lactate and potassium lactate; a hydroxyl-containing organic compound in combination with sodium lactate, potassium lactate and/or potassium acetate as well as Bio-PDO; a mixture of sodium lactate and/or potassium lactate with potassium acetate; or potassium carbonate and Bio-PDO.

For de-icing and/or anti-icing of pre-harvest fruits and vegetables, such as fruit trees or grape vines, it may be preferable to use de-icing and/or anti-icing agents of a hydroxyl-containing organic compound in combination with Bio-PDO and an organic acid salt, particularly a lactate salt.

The deicing and anti-icing compositions of the invention can contain any natural ingredients where appropriate. Natural ingredients include any natural or nature-derived ingredients similar in composition or in function to any of the ingredients listed above.

All of the compositions and methods disclosed and claimed herein can be made and executed without undue experimentation in light of the present disclosure. While the compositions and methods of the present disclosure have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents, which are chemically related, may be substituted for the agents described herein while the same or similar results would be achieved. All such similar substitutes and modifications apparent to those skilled in the art are deemed to be within the spirit, scope, and concept of the invention as defined by the appended claims.

EXAMPLES

The present invention is further defined in the following Examples. It should be understood that these Examples, while indicating preferred embodiments of the invention, are given by way of illustration only. From the above discussion and these Examples, one skilled in the art can ascertain the preferred features of this invention, and without departing from the spirit and scope thereof, can make various changes and modifications of the invention to adapt it to various uses and conditions.

Example 1

| Aircraft Deicing Fluid | |
| --- | --- |
| Ingredients: | % Wt. |
| Bio-PDO | 92 |
| Water | 7.14 |
| Polyethylene glycol ether | 0.2 |
| EO/PO alkoxylate | 0.2 |
| KOH (50% solution) | .06 |
| Sandocorin 8132C | 0.4 |

Example 2

Aircraft Deicing Fluid

| Ingredients: | % Wt. |
| --- | --- |
| Bio-PDO | 45.5 |
| Water | 53.165 |
| Tolytriazole | 0.4 |
| Silicon anti-foamer | 0.2 |
| Potassium Hydroxide | .035 |
| Triethanolamine | 0.3 |
| Sodium arylalkyl sulfonate | 0.4 |

Example 3

Aircraft runway deicing composition

| Ingredient | Wt, % |
| --- | --- |
| Alkali metal carboxylate | 20-25% |
| Alkali earth metal carboxylate | 1-15% |
| Bio-PDO | 1-35% |
| Alkali metal phosphate | 0.01-1% |
| Alkali metal silicate | 0.01-1% |
| Triazole | 0.01-1% |

Example 4

Aircraft runway deicing composition

| Ingredient | Wt, % |
| --- | --- |
| Alkali metal carboxylate | 1-40% |
| Alkali earth metal carboxylate | 1-25% |
| Bio-PDO | 1-35% |
| Alkali metal phosphate | 0.01-1% |
| Alkali metal silicate | 0.01-1% |
| Triazole | 0.01-1% |
| Water | q.s. to 100% |

Example 5

Deicer/anti-icer for aircraft

| Ingredient | Wt, % |
| --- | --- |
| Water | 41% |
| Bio-PDO | 50% |
| Polysaccharide | 3% |
| Corrosion inhibitors | 6% |

Example 6

Deicers for polyurethane foam-lined LPG tanks

| Ingredient | Wt, % |
| --- | --- |
| Isopropanol | 40% |
| Bio-PDO | 60% |

Example 7

Liquid Carboxylate Deicer Composition

The liquid deicer compounds suitable for roadways, runways, and bridges include: (a) aqueous carboxylate salt of alkali metal, especially as formate, propionate, and/or lactate; (b) corrosion inhibitors for protection of galvanized steel; (c) auxiliary corrosion inhibitors for nonferrous metals, esp. Al alloys; and (d) optional Bio-PDO, The corrosion inhibitor is preferably a polyvalent metal compd., esp. La acetate hydrate or a mixed lanthanide salt sol. in water, or optionally a Mg-ion compd. and/or a sulfide salt. The deicer optionally includes 50-10,000 ppm of tolyltriazole as auxiliary inhibitor for nonferrous metal surfaces. The typical aqueous deicer contains potassium acetate 50%, tolyltriazole 0.15-0.75%, lanthanide nitrate hexahydrate 1.0-3.0%, and trimercaptotriazine tri-Na salt 10.10-0.75%, water q.s. to 100%.

Example 8

Water-Activated, Exothermic Chemical Deicing Formulation

Deicing compositions are provided for removing ice from a surface which include either succinic acid or succinic anhydride, or both, and a neutralizing base such as sodium hydroxide, potassium hydroxide, or ammonium hydroxide wherein the deicing compositions when mixed with water produce succinate salts in a reaction that rapidly releases sufficient heat to melt the ice on the surface and the succinate salts act as a deicer and freeze point depressant. The deicing compositions may further include Bio-PDO which inhibits reformation of the ice on the deiced surface. The deicing compositions are suitable and effective for airport applications in which corrosion of aircraft alloys and concrete runways are of concern.

Example 9

Anti-Icing Fluid or Deicing Fluid

The title non-electrolytic, non-toxic, biodegradable anti-icing or deicing composition comprises: (a) water; (b) a nontoxic freeze point depressant selected from the group consisting of C2-6 monohydric alcohols, Bio-PDO, mono-Me or Et ethers of C3-12 polyhydric alcohols or mixtures thereof, (c) a nontoxic thickener. The composition is a continuous single phase liquid that exhibits pseudoplasticity, and is useful on the surfaces of, for example, aircraft, airport pavements, roadways, walkways, bridges, entrances, structures, canals, locks, components, vessels, nautical components, railroad switches, and motor vehicles. A typical composition contained water, Bio-PDO™ and/or propanol and xanthan.

What is claimed is:

1. A method of reducing the anthropogenic $CO_2$ emission of a deicing or anti-icing composition upon biodegradation, the method comprising:
   preparing a deicing or anti-icing composition comprising a glycol wherein said glycol is a biologically-derived, biodegradable 1,3-propanediol, and wherein said biologically-derived, biodegradable 1,3-propanediol exhibits no anthropogenic $CO_2$ emission upon biodegradation, and
   applying said deicing or anti-icing composition to a surface whereby said deicing or anti-icing composition biodegrades;

wherein the reduction of anthropologic $CO_2$ emission is compared to the anthropologic $CO_2$ emission of a deicing or anti-icing composition not comprising biologically-derived, biodegradable 1,3-propanediol.

2. The method of claim 1 wherein said deicing or anti-icing composition comprises a liquid.

3. The method of claim 1 wherein said deicing or anti-icing composition comprises a solid.

4. The method of claim 1 wherein said surface is selected from the group consisting of roadways, runways, aircraft, airport pavements, bridges, walking bridges, entrances, structures, pre-harvest fruit or vegetables, canals, locks, components, vessels, nautical components, railroad switches and motor vehicles.

5. The method of claim 1 wherein said glycol comprises at least 5% biobased carbon.

6. The method of claim 1 wherein said glycol comprises at least 50% biobased carbon.

7. The method of claim 1 wherein said glycol comprises 100% biobased carbon.

8. The method of claim 1 wherein said biologically-derived, biodegradable 1,3-propanediol has a peroxide concentration of less than about 100 ppm.

9. The method of claim 1 wherein said biologically-derived, biodegradable 1,3-propanediol has a concentration of carbonyl groups of less than about 10 ppm.

10. The method of claim 1 wherein said biologically-derived, biodegradable 1,3-propanediol has a concentration of total organic impurities of less than about 400 ppm.

* * * * *